(12) United States Patent
Kreutzer et al.

(10) Patent No.: US 10,086,488 B2
(45) Date of Patent: Oct. 2, 2018

(54) INHERENTLY RIGID TELESCOPIC PROTECTIVE COVER

(71) Applicant: ARNO ARNOLD GMBH, Obertshausen (DE)

(72) Inventors: Thomas Kreutzer, Obertshausen (DE); Thomas Christlieb, Obertshausen (DE); Alexander Grimm, Obertshausen (DE); Maximilian Roehnert, Obertshausen (DE); Tatjana Bock, Obertshausen (DE); Peter Weise, Obertshausen (DE); Josef Gawlik, Obertshausen (DE)

(73) Assignee: ARNO ARNOLD GMBH, Obertshausen (DE)

( * ) Notice: Subject to any disclaimer, the term of this patent is extended or adjusted under 35 U.S.C. 154(b) by 0 days.

(21) Appl. No.: 14/895,145

(22) PCT Filed: Jun. 3, 2014

(86) PCT No.: PCT/EP2014/061429
§ 371 (c)(1),
(2) Date: Dec. 1, 2015

(87) PCT Pub. No.: WO2014/195283
PCT Pub. Date: Dec. 11, 2014

(65) Prior Publication Data
US 2016/0101495 A1 Apr. 14, 2016

(30) Foreign Application Priority Data
Jun. 5, 2013 (DE) .................... 10 2013 210 407

(51) Int. Cl.
*B23Q 11/08* (2006.01)

(52) U.S. Cl.
CPC ........ *B23Q 11/0825* (2013.01); *B23Q 11/085* (2013.01); *B23Q 2011/0808* (2013.01)

(58) Field of Classification Search
CPC .............. B23Q 11/0825; B23Q 11/085; B23Q 2011/0808; F16P 3/02
(Continued)

(56) References Cited

U.S. PATENT DOCUMENTS

| 2007/0230836 A1 | 10/2007 | Schirling |
| 2013/0186577 A1* | 7/2013 | Mang ................. B23Q 11/0825 160/223 |
| 2016/0101495 A1* | 4/2016 | Kreutzer ............ B23Q 11/0825 160/131 |

FOREIGN PATENT DOCUMENTS

| CN | 2486759 Y | 4/2002 |
| DE | 20318880 U1 | 3/2004 |

(Continued)

OTHER PUBLICATIONS

PCT English Langauge Translation of the International Preliminary Report on Patentability, PCT/EP2014/061429, dated Dec. 17, 2015.
(Continued)

*Primary Examiner* — Katherine W Mitchell
*Assistant Examiner* — Abe Massad
(74) *Attorney, Agent, or Firm* — Quarles & Brady LLP (57) ABSTRACT

The invention relates to a protective cover comprising a plurality of protective cover segments (1), which can be moved telescopically against one another and which have a covering leg (2) and a supporting leg (3), and comprising a connecting element or bellows (4). When the protective cover is telescopically extended, an elastic restoring element produces a torque (M) and transfers said torque to the supporting leg (3). The invention is characterized in that the elastic restoring element is an integral component of the connecting element (4) in that the connecting element (4)

(Continued)

has flexural rigidity and is connected to the supporting leg (3) in a planar manner along a height portion (h) of the supporting leg (3). Owing to the invention, an additional elastic restoring element and the attachment thereof to the supporting leg are no longer necessary. Thus, the compressed size, the weight and the production complexity of the protective cover can be reduced, and the leak tightness and reliability of operation are improved.

12 Claims, 6 Drawing Sheets

(58) Field of Classification Search
USPC .................................................. 160/202, 223
See application file for complete search history.

(56) References Cited

FOREIGN PATENT DOCUMENTS

| DE | 103 08 024 A1 | 9/2004 |
| DE | 10 2005 013496 A1 | 10/2006 |
| DE | 10 2010 045 810 | 3/2012 |
| DE | 10 2012 103006 A1 | 12/2012 |
| DE | 102011114177 A1 * | 3/2013 |
| EP | 1 842 620 A1 | 10/2007 |
| JP | H10180587 A | 7/1998 |
| JP | 2007144534 | 6/2007 |
| JP | 2008012639 A | 1/2008 |
| JP | 2008080463 A | 4/2008 |
| JP | 4833013 B2 * | 12/2011 |
| WO | 2004/074736 | 9/2004 |
| WO | 2012/041293 | 4/2012 |
| WO | 2012/175232 | 12/2012 |

OTHER PUBLICATIONS

International Search Report dated Sep. 19, 2014 for International Application No. PCT/EP2014/061429.
State Intellectual Property Office of People's Republic of China, First Office Action and Search Report, Application No. 201480032508.8, dated Nov. 3, 2016.
Japan Patent Office, Notification of Reason(s) for Refusal, Application No. P2016-517265, dated Apr. 14, 2017.

* cited by examiner

INHERENTLY RIGID TELESCOPIC PROTECTIVE COVER

CROSS-REFERENCE TO RELATED APPLICATIONS

This application represents the national stage entry of PCT International Application No. PCT/EP2014/061429 filed Jun. 3, 2014 and claims priority to German Patent Application No. 10 2013 210 407.3 filed Jun. 5, 2013. The contents of this application are hereby incorporated by reference as if set forth in their entirety herein.

The invention relates to a protective cover according to the preamble of patent claim 1.

In machine tools, for example, protective covers of the mentioned kind are used to secure mobile parts such as drives and the like against unintentional access of a user of the machine and to additionally close the working space of the machine tool in such a way that no chips, liquid media or other parts and particles can enter or exit in a manner that would endanger the user and/or pollute other machine areas.

For this purpose, common generic protective covers have protective cover segments in the form of substantially L-shaped metal sheet elements, which can be moved telescopically against one another and engage behind one another with one of their legs, thus forming a substantially closed and mobile cover that can be changed in length.

Since the cover legs engaging behind one another simply continue to rest on one another in a largely loose fashion, it is oftentimes impossible to achieve a sufficiently leak-tight closure without having to take constructively elaborate additional measures. This is why generic protective covers are usually additionally provided with bellows at their rear side in order to ensure a comparatively leak-tight closure, the bellows having to be connected to the metal sheet elements of the protective cover in a suitable manner.

Also, protective covers are known in which the rearward bellows is attached to tabs, for example, that are molded to the metal sheet elements of the protective cover. For this purpose, however, slots may have to be die-cut into the bellows, said slots being penetrated by the tabs of the metal sheet elements so as to attach the bellows to the metal sheet elements of the protective cover. This may lead to weak spots with respect to the leak-tightening effect of the protective cover or of the bellows because media or pollutants can penetrate the slots in the bellows.

To improve the leak tightness and the uniform cohesion of the metal sheet elements resting against one another, it is known from WO 2012/175232 A1 and further from DE 10 2005 013 496 B4, for example, to arrange resilient restoring elements between the metal sheet elements in such a manner that suitable restoring forces and corresponding torques are generated and transferred to the metal sheet elements. Among other things, the restoring forces and torques are supposed to have the effect that the overlapping covering legs of the protective cover no longer rest loosely on top of one another but are pressed onto one another by a contact pressing force.

However, the restoring elements additionally necessary for this purpose and their attachment to the metal sheet elements cause additional effort for production and assembly. Moreover, the restoring elements and their attachment to the metal sheet elements increase the compressed size of the protective cover when it is to be pushed together into its minimum length.

All these facts make protective covers of this kind difficult to produce and comparatively expensive. Ultimately, the weight of the protective cover is increased as well, which means that protective covers of greater length cannot be moved with the necessary speed and acceleration because of their increased weight.

Starting from this state of the art, the object of the present invention thus is to provide a protective cover that ensures a secure and leak-tight closure of workspaces to be separated in particular in a machine tool at a comparatively low weight and comparatively low production costs.

This object is attained by a protective cover according to the teaching of patent claim 1. Advantageous embodiments of the invention are the subject-matter of the dependent claims.

In an initially known manner, the protective cover in accordance with the present invention comprises a plurality of substantially L-shaped protective cover segments, each having a covering leg and a supporting leg. Said protective cover segments are arranged in relation to one another in such a manner that they can be moved telescopically against one another, the covering legs of adjacent protective cover segments coming to rest on each other, thus forming a substantially completely closed surface. Furthermore, at least one belt-shaped or web-shaped flexible connecting element is provided that connects the supporting legs of the protective cover segments like an accordion in the manner of a bellows.

In an initially equally known manner, at least one elastic restoring element is arranged on the supporting leg of the respective protective cover segment in such a manner that it generates and transfers a torque to the supporting leg when the protective cover is telescopically extended.

According to the invention, however, the protective cover is characterized in that the elastic restoring element is an integral component of the connecting element. In other words, the function of the elastic restoring element is performed by the connecting element or bellows itself in the invention, which means that the restoring element needed as an additional component in the state of the art and the attachment thereof are no longer necessary. This is achieved in that the connecting element is realized in the shape of an inherently rigid belt or a flexurally rigid web, the belt or web being connected to the supporting leg of the protective cover segment in a planar manner along a height portion of the supporting leg.

Owing to the use of an inherently rigid belt as the connecting element and owing to the fact that its connection to the supporting leg does not take place only in one point or in a line but encompasses an area along a height portion of the supporting leg, both the elastic restoring element that is additionally required in the state of the art and the attachment thereof to the supporting leg as well as the additional connection necessary in the state of the art between the protective cover segments and the flexible connecting element or bellows are no longer necessary at all.

Instead of the (no longer necessary) restoring element, the connecting element itself, which is realized as an inherently rigid belt, generates the desired forces, torques and contact pressing forces between the covering legs of the protective cover segments according to the invention. For this purpose, when the protective cover is telescopically extended, the connecting element induces a torque onto the protective cover segment because of the flexural rigidity or inherent rigidity of the connecting element and because of its connection to the supporting leg encompassing an area, said torque trying to tilt the protective cover segment. Thus, the torque causes the edges of the telescopically overlapping covering legs to be pressed onto the surfaces of the adjacent covering legs, resulting altogether in a secure and leak-tight closure of the protective cover.

Owing to the invention, the connecting element or bellows does not only fulfill the sealing function and the additional function of the spring elements (no longer necessary with the invention) between the protective cover segments but also additionally generates a torque that has a stabilizing effect on the protective cover segments, thus improving the smooth motion and the sealing effect of the protective cover segments.

The design and the material selection for the connecting element and the design of the planar attachment of the connecting element, i.e. the attachment encompassing an area, along a height portion of the supporting leg is basically optional as long as the connecting element can transfer the force necessary for smooth telescopic extension to the protective cover segments on the one hand and the desired torque can be generated and transferred to the protective cover segment by the connecting element when the protective cover is extended on the other hand.

According to a first preferred embodiment example of the invention, the connecting element is attached to the supporting leg at the two planar sides of the supporting leg along substantially equally large height portions. This embodiment allows particularly simple production of the connection between the connecting element and the protective cover segments. At the same time, the desired stabilizing effect for the protective cover segments is realized with this embodiment in that the planar torque-transferring attachment of the connecting element to the protective cover segments together with the inherent rigidity of the material of the connecting element leads to torques being induced in the connecting element and being transferred to the protective cover segments during telescopic extension of the protective cover and because of the tilting of the mutually engaging protective cover segments due to geometry, said torques resulting in the desired contact pressing force between adjacent protective cover segments.

Another embodiment of the invention provides that the height portion for attachment of the connecting element to the planar side of the supporting leg that faces toward the covering leg is larger than the height portion for attachment of the connecting element to the planar side of the supporting leg that faces away from the covering leg. This embodiment includes in particular other embodiments, which will be described below and in which the height portion for attachment of the connecting element to the side of the supporting leg that faces away from the covering leg is zero or in which the connecting element is not attached to the latter side of the supporting leg at all but only to the side of the supporting leg that faces toward the covering leg.

In particular, this embodiment has the advantage that when the protective cover is telescopically extended, substantially higher torques are generated by the protective cover and are transferred to the protective cover segments because of the highly asymmetrical deformation of the connecting element during extension that is achieved with this embodiment, which results in increased leak tightness and an even better mutual wiping effect between the covering legs of the protective cover, which rest on each other.

The manner in which the different sizes of the height portions for attachment of the connecting element to the two planar sides of the supporting leg or, as the case may be, for attachment of the connecting element to only one planar side of the supporting leg are constructively achieved is basically optional as long as the attachment allows the necessary forces and torques to be transferred.

According to another embodiment, however, it is provided that the supporting leg has at least one, but preferably a plurality of preferably circular or elliptical openings within the height portion for attachment of the connecting element to the supporting leg, which openings can be utilized to attach the connecting element to the supporting leg. Attaching the connecting element at or in openings of the supporting leg is, first of all, constructively especially simple and can thus be realized at low cost.

Against this background, another embodiment of the invention provides that two flanks of the connecting element in the area of the supporting leg penetrate the at least one opening formed in the supporting leg and are connected to each other within the opening. The two flanks of the connecting element are connected within the opening preferably in a material-bonded manner, in particular by welding, for example by ultrasonic welding.

In this way, the connecting element can be attached to the supporting leg in a simple and cost-effective manner without requiring additional attachment materials or attachment elements.

According to another embodiment, an attachment strip that surrounds both planar sides of the supporting leg is arranged on the supporting leg in the area of the at least one opening, the two flanks of the attachment strip penetrating the at least one opening and again being preferably connected to each other as described above in a material-bonded manner within the at least one opening. Moreover, the connecting element is connected, again preferably welded, to the attachment strip in a planar manner along a height portion of the supporting leg and of the attachment strip. This embodiment leads to an especially robust attachment of the connecting element to the supporting leg and to good force and torque transfer between the connecting element and the supporting leg due to the large-area welding possible in this case between the connecting element and the attachment strip, which thus induces forces and generated torques across an equally large area into the supporting leg.

Another embodiment provides that an attachment strip is arranged on the planar side of the supporting leg that faces away from the covering leg in the area of the at least one opening in the supporting leg. The attachment strip and the flank of the connecting element that faces toward the covering leg penetrate the at least one opening and are connected to each other preferably in a material-bonded manner within the at least one opening.

This embodiment leads to a simple attachment of the connecting element to the supporting leg via (minimum) only one attachment strip per protective cover segment, said attachment strip covering all openings formed in a protective cover segment. Furthermore, the thickness and compressed size of the protective cover in the compressed state are reduced owing to the attachment strip that is provided on only one side of the supporting leg.

According to another embodiment, it is provided that an attachment element, preferably a rivet, is arranged in the at least one opening of the supporting leg on the planar side of the supporting leg that faces away from the covering leg. The attachment element and the flank of the connecting element that faces toward the covering leg both penetrate the at least one opening and are connected to each other within the opening, preferably in a material-bonded manner as in the embodiments described above.

Another embodiment for attaching the connecting element to the supporting leg of the protective cover segment provides that the connecting element is connected to the supporting leg on the planar side of the supporting leg that faces toward the covering leg by means of an adhesive tape covering a height portion.

This embodiment has the advantage of a simple, space-saving and large-area attachment of the connecting element 5 to the supporting leg. For example, the adhesive tape can be a double-faced adhesive tape or a hot-melt film tape coated on one side, which is glued to the supporting leg with the hot-melt-coated side and is connected, preferably welded, to the connecting element on the uncoated backside.

The material of the connecting element or bellows of the protective cover according to the invention is basically optional as long as the bending moments (by means of bending the belt-shaped or web-shaped connecting element) necessary for generating and transferring a torque to the protective cover segments can be generated, in other words, as long as it is a belt-shaped or web-shaped material that has a certain inherent or flexural rigidity, i.e. that is not substantially limp (such as in case of a purely textile material or thin films).

However, a preferred embodiment of the invention provides that the connecting element is made of an inherently rigid polymer web material, preferably of polypropylene. Polymer materials of this kind, such as certain thermoplastics, are cost-efficient and, in particular if polypropylene is used, are furthermore highly resistant to aqueous media, acids, alkalis, oils and other chemicals, which is an additional advantage for the intended use as a protective cover for machine tools. The material thickness of the connecting element preferably ranges from 0.3 to 1.5 mm, particularly preferably from 0.5 to 1.0 mm. These thicknesses have proved practical with regard to operational reliability on the one hand and with regard to the required bending moments in the web material of the connecting element or bellows on the other hand.

In the following paragraphs, the invention will be described in more detail based on the drawings, which merely represent embodiment examples.

Figure 1:
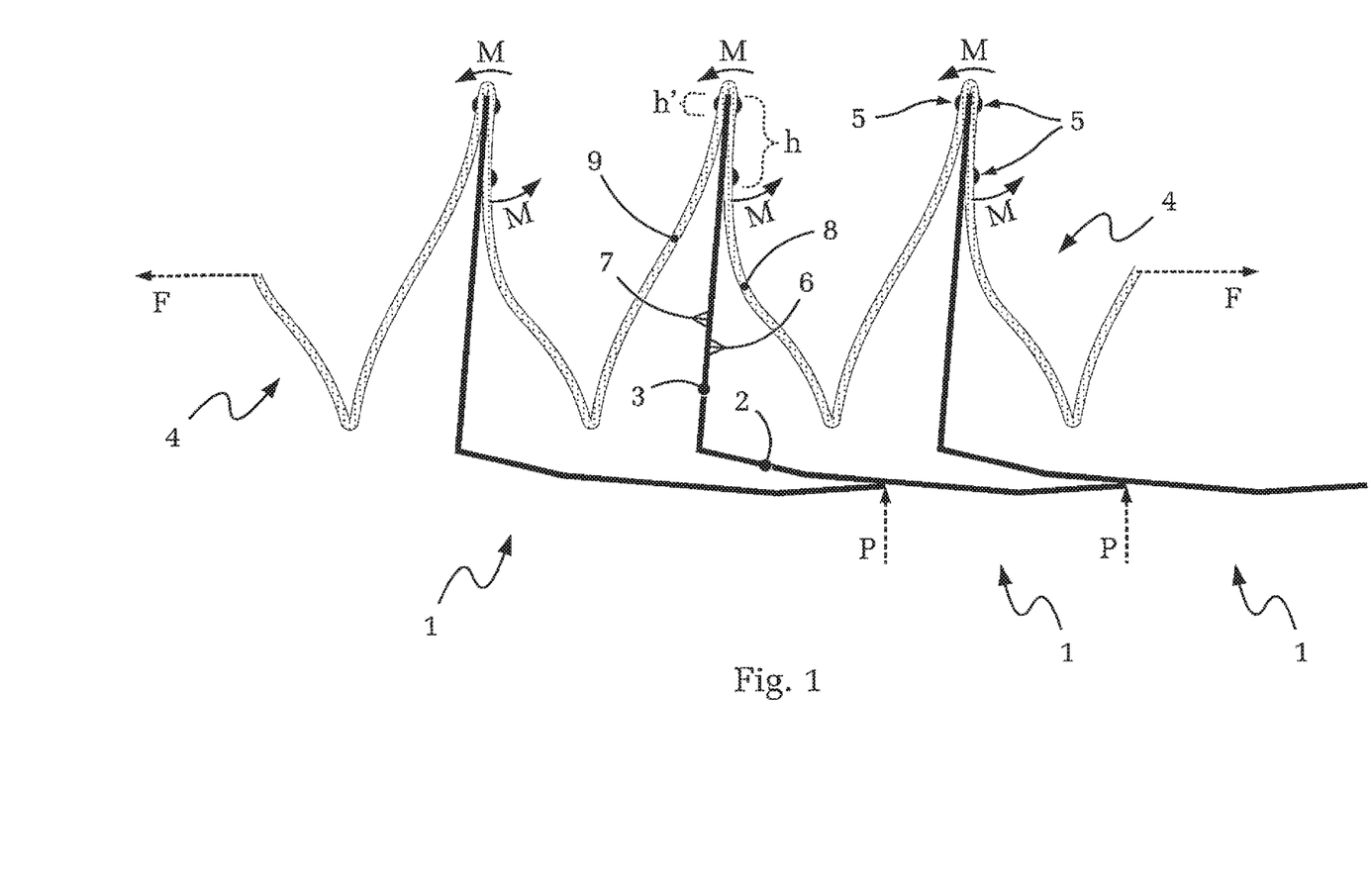
FIG. 1 shows a schematic illustration of a protective cover according to an embodiment of the present invention in a lateral view.

FIG. 1 shows a schematic illustration of a section of a protective cover according to an embodiment of the present invention. Immediately visible are three protective cover segments 1 that can be telescopically moved against and into one another in the horizontal direction in reference to the drawing. Each of the protective cover segments 1 has a covering leg 2 and a supporting leg 3.

In a per se initially known manner, the protective cover segments 1 are connected to one another via a web-shaped connecting element or bellows 4.

However, according to the invention, the material of the connecting element or bellows 4 is inherently rigid or flexurally rigid. Moreover, the bellows 4 is attached to the supporting legs 3 in such a manner that height portions h and h' are created, along or within which the bellows 4 is connected to the respective supporting leg 3 in a planar manner.

The rivets 5 indicated in FIG. 1 only serve to schematically visualize a connection between the bellows 4 and the supporting leg 3, which means that they are a possible but not a particularly preferred embodiment of this connection.

It is visible in FIG. 1 that the height portion h on the right side as shown in the drawing, i.e. on the planar side 6 of the supporting leg 3 that faces toward the covering leg 2, is substantially larger than the height portion h' on the left side as shown in the drawing, i.e. on the planar side 6 of the supporting leg 3 that faces away from the covering leg 2. With respect to the flanks 8 of the bellows 4 on the right side in reference to the drawing, this leads to larger lever arms and also to a greater degree of bending of the flanks 8 of the bellows 4 on the right side in reference to the drawing as compared to the flanks 9 on the left side in reference to the drawing. In case of the latter, both the degree of bending and the lever arm of attack at the supporting leg 3 are smaller.

The greater degree of bending of the flanks 8 of the inherently rigid bellows 4 on the right side in reference to the drawing and the larger height portion h for connecting the bellows 4 and the supporting leg 3 and the consequently greater lever arm there lead to a torque M being effectively generated in the flanks 8, 9 of the bellows 4 because of the extending force F, said torque being transferred to the respective protective cover segment 1 via the connection 5 between the bellows 4 and the supporting leg 3. In other words, this means that the bellows 4 tries to twist the respective protective cover segment 1 to the left in reference to the drawing, and it does so with increasing strength as the bellows 4 is extended further by means of the force F.

In addition to a very uniform distribution of the extending force F across the individual members or protective cover segments 1 of the protective cover, a contact pressing force P is thus generated in the area of the mutual linear contact between the covering legs 2, said contact pressing force P pressing the edges of the covering legs 2 onto the surfaces of the adjacent covering legs 2. All in all, improved leak tightness, stability and reliability of operation of the protective cover according to the invention are achieved as desired in this manner without restoring spring elements or the like having to be additionally provided or attached between the supporting legs 3 of the protective cover for this sole purpose as it is the case in the state of the art.

Since the restoring spring elements and attachment thereof to the protective cover segments are no longer necessary, the additional compressed size that would be added to each protective cover segment by these elements is eliminated as well. This leads to a significant reduction of the compressed size of the protective cover in the compressed state as well as to a reduction of the weight of the protective cover, which is of decisive importance in case of high moving speeds or accelerations.

Figure 2:
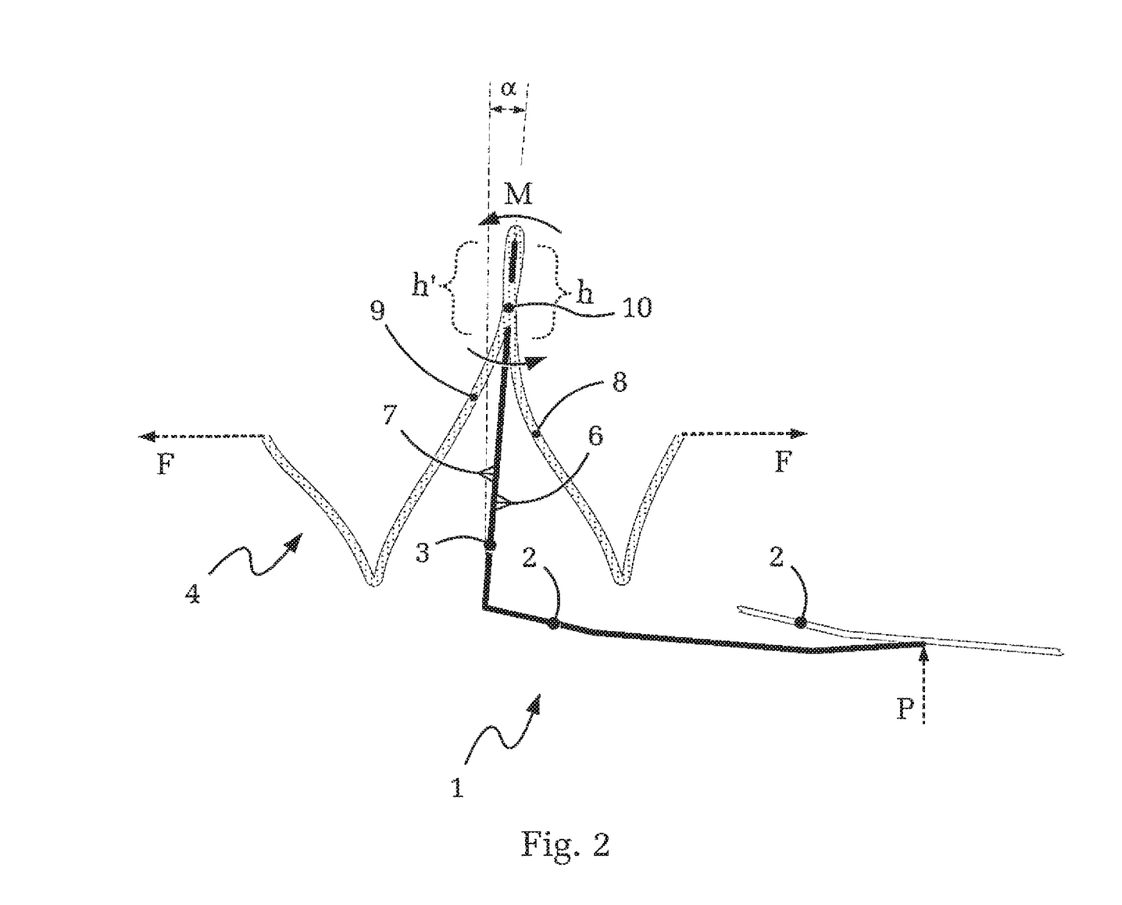
FIG. 2 shows an illustration corresponding to FIG. 1 of a segment of a protective cover according to another embodiment.

FIG. 2 shows a segment of a protective cover according to another embodiment of the invention. In this embodiment, a number of preferably circular or elliptical openings 10 are formed in the supporting leg 3 within the height portions h and h' for attachment of the bellows 4 along the transverse direction of the protective cover (vertical to the drawing plane of FIG. 2) for the purpose of attaching the bellows 4 to the supporting leg 3.

The two flanks 8 and 9 of the bellows 4 are connected, for example ultrasonically welded, to each other in the area of the openings 10, resulting in a form-fitting connection between the bellows 4 and the supporting leg 3 along the height portions h and h'. In this embodiment, the height portions h and h' on the left and on the right side in reference to the drawing are about the same height. Still, in this embodiment too, the bellows 4 generates a counter-clockwise torque M in reference to the drawing because the protective cover segments 1 are tilted a during operation of the protective device, said torque M again having the desired result that the edges of the covering legs 2 of the protective cover segments 1 are pressed onto the adjacent covering legs 2 with the force P.

Figure 3:
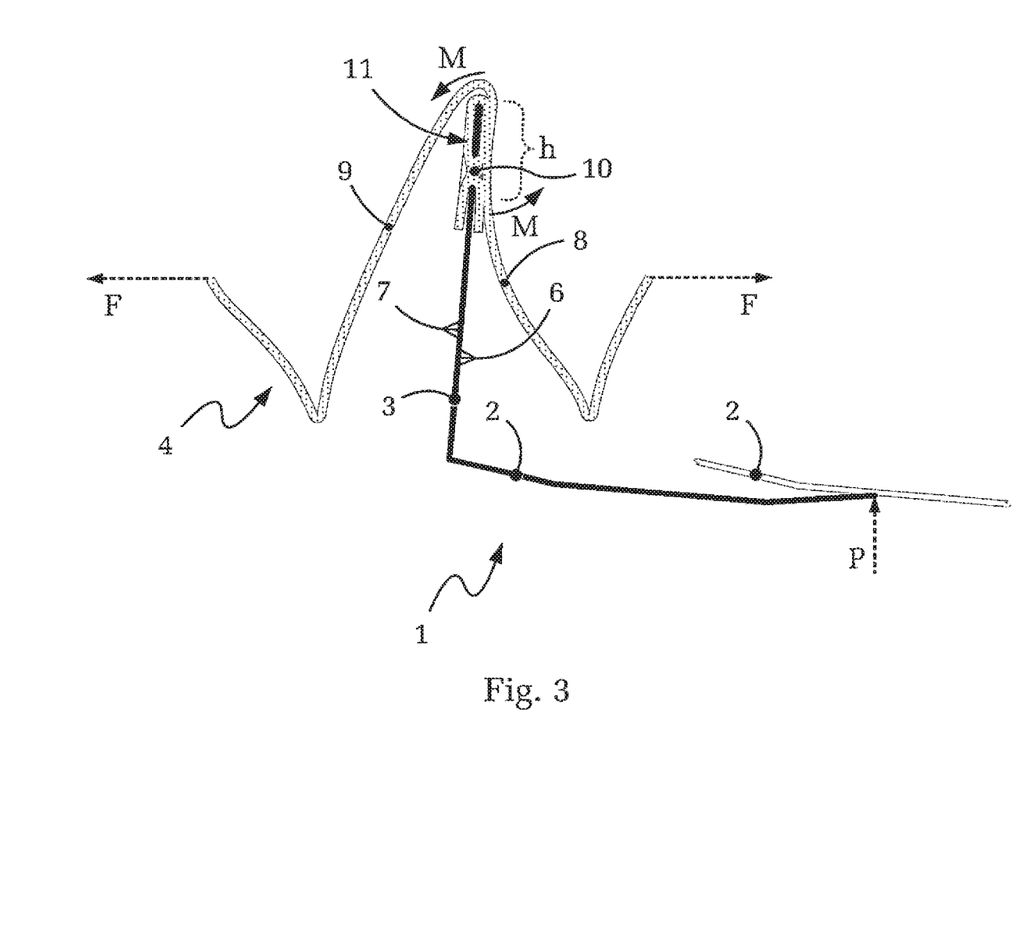
FIG. 3 shows an illustration and view corresponding to FIG. 2 of a segment of a protective cover having attachment strips on both sides.
Figure 4:
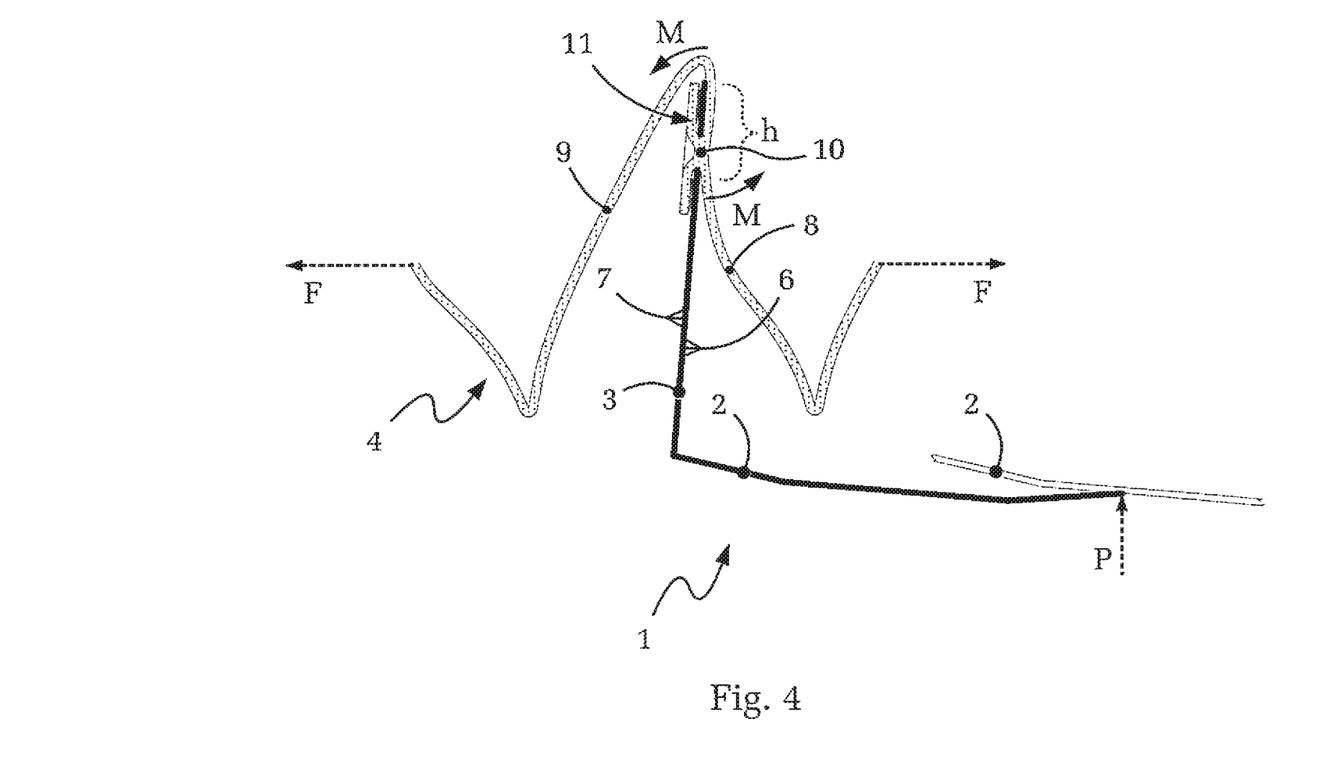
FIG. 4 shows an illustration and view corresponding to FIGS. 2 and 3 of a segment of a protective cover having an attachment strip on one side.

FIGS. 3 and 4 show further embodiments, in which the connection between the bellows 4 and the supporting leg 3 is achieved by means of an attachment strip 11 that is arranged on the supporting leg 3 within the height portion h and is itself connected to the bellows 4. In this way, a connection is formed between the bellows 4 and the supporting leg 3 or the protective cover segment 1 in the height portion h, which encompasses only the flank 8 of the bellows 4 on the right side in reference to the drawing. In this way, as described before with regard to FIG. 1, a corresponding effective torque M is generated because of the different degrees of bending of the two flanks 8, 9 of the bellows 4, said torque M trying to twist the protective cover segments 1 counter-clockwise in the desired manner, thus generating the contact pressing force P.

In the embodiment according to FIG. 3, the attachment portion 11 is folded over the upper edge of the supporting leg 3 in reference to the drawing and thus surrounds the supporting leg 3 in the area of its two planar sides 6, 7, the two sides of the attachment strip 11 being connected, preferably welded to each other, again in the area of the openings 10 of the supporting leg 3. The right flank 8 of the bellows 4 is then in turn connected, also preferably welded, to the attachment strip 11.

In the embodiment according to FIG. 4, the attachment strip 11 is arranged on only one side of the supporting leg, namely the left planar side 7 with reference to the drawing, either loosely or by adhesion, and is connected directly to the right flank 8 of the bellows 4 in reference to the drawing in the area of the openings 10. This embodiment allows in particular a smaller compressed size of the protective cover in the completely compressed state.

Figure 5:
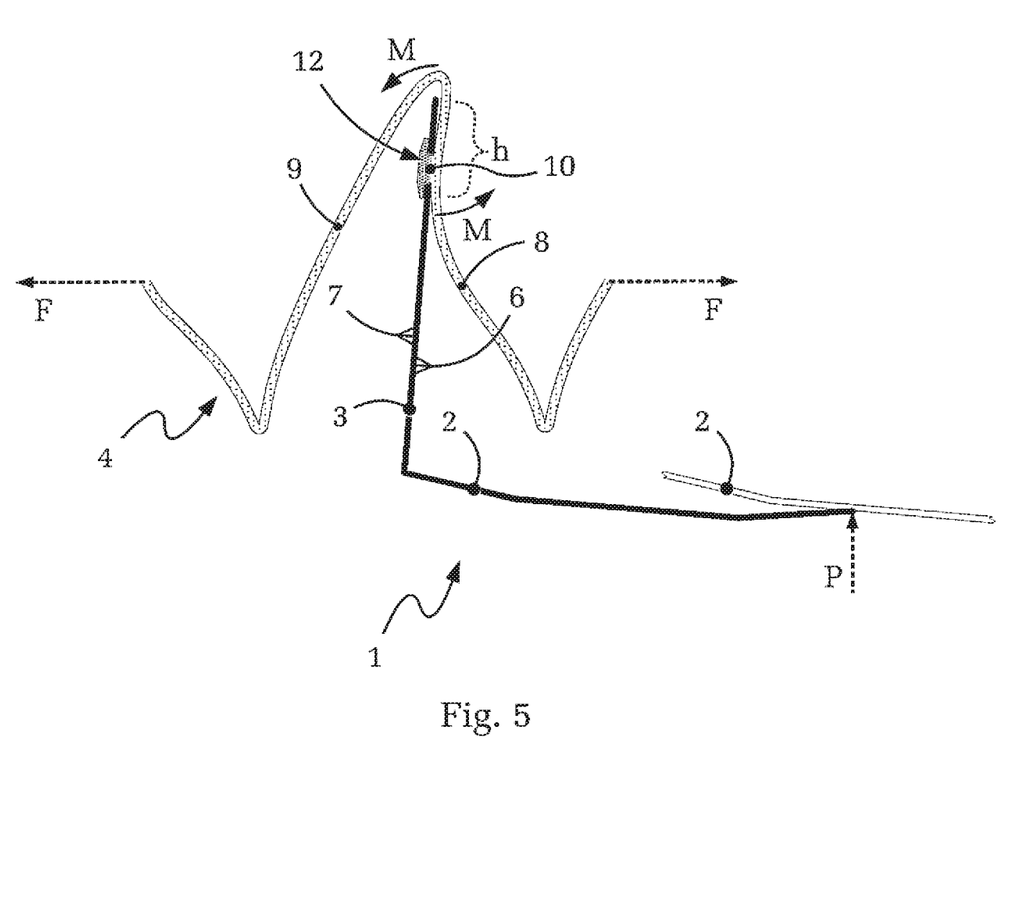
FIG. 5 shows an illustration and view corresponding to FIGS. 2 to 4 of a segment of a protective cover exhibiting a rivet attachment.

FIG. 5 shows another embodiment, which differs from the embodiment according to FIG. 4 in that instead of the attachment strip 11, rivets 12 are used to connect the right flank 8 of the bellows 4 in reference to the drawing to the supporting leg 3, said rivets 12 being material-bonded, preferably welded, to the flank 8 of the bellows 4 in the openings 10. This embodiment allows a particularly material-saving, weight-saving and space-saving attachment of the bellows 4 to the supporting leg 3, in particular when the openings 10 and the rivets 12 of adjacent protective cover segments 1 are arranged in an offset manner.

Figure 6:
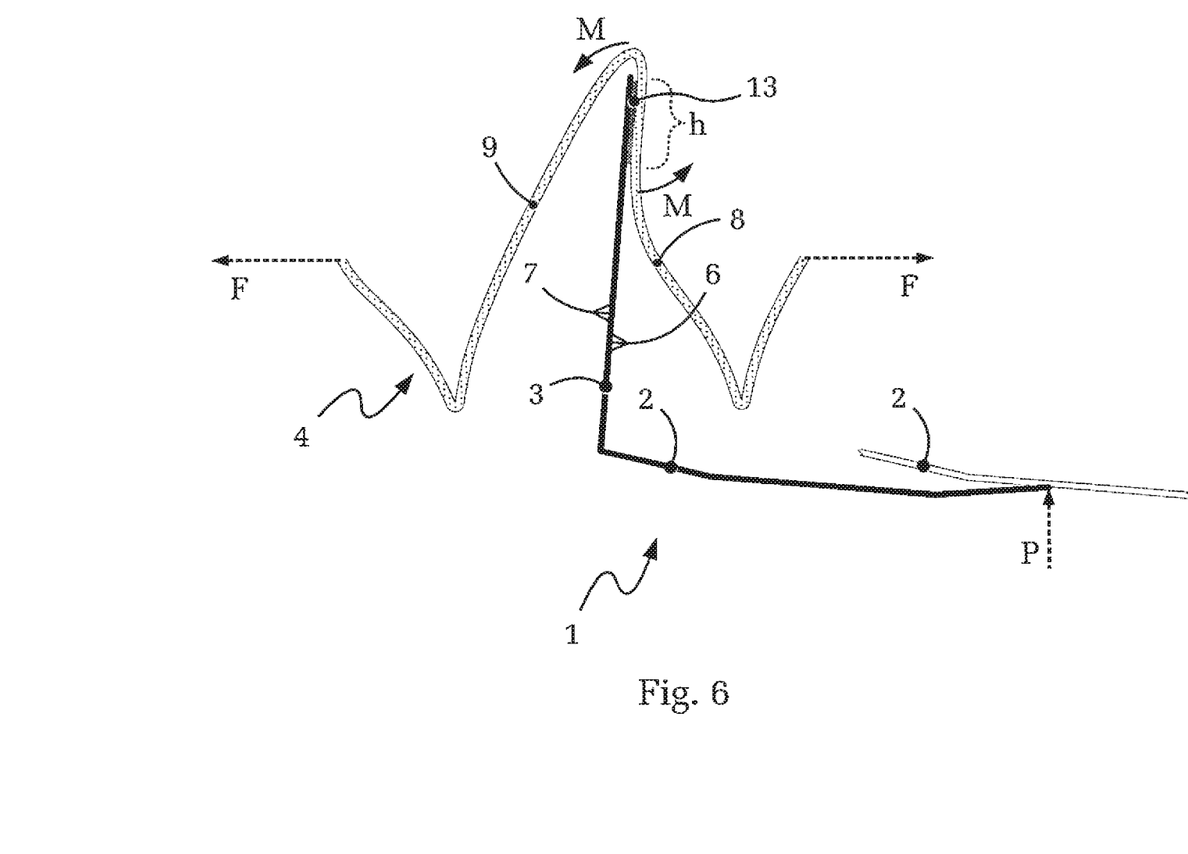
FIG. 6 shows an illustration and view corresponding to FIGS. 2 to 4 of a segment of a protective cover exhibiting an adhesive tape attachment.

In the embodiment according to FIG. 6, the right flank 8 of the bellows 4 is attached by means of an adhesive tape 13 covering the height portion h, for example by means of a double-faced adhesive tape or by means of a hot-melt film tape, which has a hot-melt coating on the left surface in reference to the drawing, for example, and is welded to the flank 8 of the bellows 4 with the backside in reference to the drawing, for example.

The invention claimed is:

1. A protective cover comprising a plurality of substantially L-shaped protective cover segments, which each have a covering leg and a supporting leg, which are arranged in relation to one another in such a manner that they can be moved telescopically against one another, the covering legs of adjacent protective cover segments coming to rest on each other, thus forming a substantially completely closed surface, and comprising at least one flexible belt or web connecting element, which connects the supporting legs of the protective cover segments like an accordion in the manner of a bellows, said connecting element comprising an inner surface facing toward the covering leg and an outer surface facing away from the covering leg,
  at least one elastic restoring element acting on each supporting leg in such a manner that a torque is generated and transferred to the supporting leg when the protective cover is telescopically extended,
  characterized in that
  the connecting element is formed of a material having a flexural rigidity selected to generate torque and at least one flank of the connecting element is coupled directly to the supporting leg in a planar manner along a height portion of the supporting leg, inducing a torque to rotate the supporting leg in a direction away from the covering leg to generate a contact pressing force in an area of mutual linear contact between adjacent covering legs to press adjacent edges thereof together without an additional elastic restoring member, and wherein the connecting element and elastic restoring element are formed as a unitary component.

2. The protective cover according to claim 1,
  characterized in that
  the connecting element is attached to the supporting leg at first and second planar sides along substantially equally large height portions.

3. The protective cover according to claim 1,
  characterized in that
  the height portion for attachment of the connecting element to a planar side of the supporting leg that faces toward the covering leg is larger than the height portion for attachment of the connecting element to a planar side of the supporting leg that faces away from the covering leg.

4. The protective cover according to claim 1,
  characterized in that
  the supporting leg has at least one opening for attaching the connecting element to the supporting leg within the height portion for attachment of the connecting element.

5. The protective cover according to claim 4,
  characterized in that
  first and second flanks of the connecting element penetrate the at least one opening formed in the supporting leg and are connected to each other within the at least one opening.

6. The protective cover according to claim 4,
  characterized in that
  in the area of the at least one opening formed in the supporting leg, an attachment strip is arranged, which surrounds first and second planar sides of the supporting leg and comprises first and second flanks that penetrate the at least one opening and are connected to each other within the at least one opening, the connecting element being connected to the attachment strip in a planar manner along a height portion of the supporting leg and of the attachment strip.

7. The protective cover according to claim 4, characterized in that
in the area of the at least one opening formed in the supporting leg, an attachment strip is arranged on a planar side of the supporting leg that faces away from the covering leg, the attachment strip and a flank of the connecting element that faces toward the covering leg penetrating the at least one opening and being connected to each other within the at least one opening.

8. The protective cover according to claim 4, characterized in that
on a planar side of the supporting leg that faces away from the covering leg, an attachment element is arranged in the at least one opening of the supporting leg, the attachment element and a flank of the connecting element that faces toward the covering leg penetrating the at least one opening and being connected to each other within the at least one opening.

9. The protective cover according to claim 3, characterized in that
on a planar side of the supporting leg that faces toward the covering leg, the connecting element is connected to the supporting leg by means of an adhesive tape covering the height portion.

10. The protective cover according to claim 1, characterized in that
the connecting element is made of a rigid polymer web material.

11. The protective cover according to claim 1, characterized in that
a material thickness of the connecting element ranges from 0.3 to 1.5 mm.

12. The protective cover according to claim 1, characterized in that
a material thickness of the connecting element ranges from 0.5 to 1.0 mm.

* * * * *

UNITED STATES PATENT AND TRADEMARK OFFICE
CERTIFICATE OF CORRECTION

PATENT NO. : 10,086,488 B2
APPLICATION NO. : 14/895145
DATED : October 2, 2018
INVENTOR(S) : Thomas Kreutzer et al.

Page 1 of 1

It is certified that error appears in the above-identified patent and that said Letters Patent is hereby corrected as shown below:

In the Specification

Column 7, Line 10, "tilted a during" should be --tilted α during--.

Signed and Sealed this
Twenty-fifth Day of December, 2018

Andrei Iancu
*Director of the United States Patent and Trademark Office*